United States Patent
Dutta et al.

(10) Patent No.: US 10,166,412 B2
(45) Date of Patent: Jan. 1, 2019

(54) SKIN LIGHTENING COMPOSITION COMPRISING 4-HEXYLRESORCINOL AND ILOMASTAT

(71) Applicant: Conopco, Inc., Englewood Cliffs, NJ (US)

(72) Inventors: Maitreyee Dutta, Bangalore (IN); Vaidehi Subhash Kale, Maharashtra (IN); Nirmala Santosh Nair, Bangalore (IN)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/539,857

(22) PCT Filed: Nov. 24, 2015

(86) PCT No.: PCT/EP2015/077410
§ 371 (c)(1),
(2) Date: Jun. 26, 2017

(87) PCT Pub. No.: WO2016/107697
PCT Pub. Date: Jul. 7, 2016

(65) Prior Publication Data
US 2017/0354835 A1    Dec. 14, 2017

(30) Foreign Application Priority Data
Dec. 30, 2014  (EP) ..................... 14200625

(51) Int. Cl.
  *A61K 8/00*     (2006.01)
  *A61Q 19/02*    (2006.01)
  *A61K 8/34*     (2006.01)
  *A61K 8/49*     (2006.01)
(52) U.S. Cl.
  CPC .............. *A61Q 19/02* (2013.01); *A61K 8/347* (2013.01); *A61K 8/492* (2013.01)
(58) Field of Classification Search
  None
  See application file for complete search history.

(56) References Cited

U.S. PATENT DOCUMENTS

| | | | |
|---|---|---|---|
| 2002/0013345 A1 | 1/2002 | Berman | |
| 2002/0120225 A1 | 8/2002 | McDaniel | |
| 2004/0219179 A1 | 11/2004 | McDaniel | |
| 2006/0074108 A1 | 4/2006 | Gupta | |
| 2006/0217690 A1 | 9/2006 | Bastin et al. | |
| 2007/0225301 A1 | 9/2007 | Weidner | |
| 2008/0193394 A1 | 8/2008 | Nam et al. | |
| 2009/0197939 A1 | 8/2009 | Walke et al. | |
| 2009/0263513 A1 | 10/2009 | Marini | |
| 2010/0158842 A1 | 6/2010 | Wille, Jr. | |
| 2010/0241059 A1 | 9/2010 | Prushinskaya et al. | |
| 2010/0278784 A1* | 11/2010 | Pojasek ............. | A61K 8/498 424/93.7 |
| 2011/0280909 A1 | 11/2011 | Moazed | |
| 2012/0052095 A1 | 3/2012 | Chaniyilparampu et al. | |

FOREIGN PATENT DOCUMENTS

| | | |
|---|---|---|
| DE | 10133196 | 1/2003 |
| EP | 2912653 | 8/2008 |
| EP | 2412701 | 2/2012 |
| EP | 2522331 | 11/2012 |
| WO | WO0219982 | 3/2002 |
| WO | WO2008079898 | 7/2008 |
| WO | WO2010044076 | 4/2010 |

OTHER PUBLICATIONS

IPRP1 in PCTEP2015078975, Jul. 4, 2017.
Lin X et al., GM6001, a broad spectrum metalloprotease inhibitor, has multiple efficacies against skin aging, Journal of Investigative Dermatology, Apr. 1, 2010, p. 1, Abstract, XP009141234, ., Nature Publishing Group, GB.
Search Report & Written Opinion in PCTEP2015077410, dated Jan. 25, 2016.
Search Report & Written Opinion in PCTEP2015078975, dated Feb. 9, 2016.
Search Report and Written Opinion in EP14200619, dated Jun. 24, 2015.
Search Report and Written Opinion in EP14200625, dated Jun. 26, 2015.
Co-Pending Application; entitled A Skin Lightening Composition Comprising Niacinamide and Ilomastat; filed on Jun. 26, 2017.
IPRP1 in PCT2015077410, Jul. 4, 2017 (references mentioned therein previously submitted).

* cited by examiner

*Primary Examiner* — David Browe
(74) *Attorney, Agent, or Firm* — Edward A. Squillante, Jr.

(57) ABSTRACT

The present invention is in the field of personal care compositions; in particular skin lightening compositions. A more effective way to reduce melanin content in melanocytes remains to be desired. It has been found that 4-hexylresorcinol in combination with MMP inhibitor galardin synergistically reduces melanin content in melanocytes. The invention thus relates to a composition comprising a synergistic combination of 4-hexylresorcinol and galardin for use in skin lightening. Thus the composition, when applied topically over an appropriate length of time in-vivo, may be used to lighten the skin, or to reduce age spots or freckles.

6 Claims, No Drawings

SKIN LIGHTENING COMPOSITION COMPRISING 4-HEXYLRESORCINOL AND ILOMASTAT

FIELD OF THE INVENTION

The present invention is in the field of personal care compositions; in particular skin lightening compositions.

BACKGROUND OF THE INVENTION

Most people are concerned with the degree of pigmentation of their skin. For example, people with age spots or freckles may wish such pigmented spots to be less pronounced. Others may wish to reduce the skin darkening caused by exposure to sunlight or to lighten their natural skin colour. To meet this need, many attempts have been made to develop products that reduce the pigment production in the melanocytes. However, the substances identified thus far tend to have either low efficacy or undesirable side effects, such as, for example, toxicity or skin irritation. Therefore, there is a continuing need for new cosmetic skin lightening agents, with improved overall effectiveness.

Conventional skin lightening compositions are based on use of skin lightening agents that are believed to control dispersion of melanin or inhibit tyrosinase. These skin-lightening agents include niacinamide, carboxylic acids like azelaic acid and kojic acid, plant extracts and hydroquinone etc. Hexylresorcinol, is one such widely used skin lightening agent in compositions for topical application.

The ability of hexylresorcinol to target pathways in the skin that lead to hyperpigmentation has propelled it into the skin lightening ingredient category. It is also thought that hexylresorcinol has more benefits as well, including an ability to reduce the appearance of fine lines and wrinkles, increase protection against UVB and UVA rays, and improve the skin's barrier against pollution and sun exposure.

It has been demonstrated that hexylresorcinol reduces melanin content in melanocytes by its ability to directly inhibit tyrosinase enzyme activity, which in turn is believed to be largely responsible for its ability to provide skin lightening efficacy.

However, a more effective way to reduce melanin content in melanocytes remains to be desired.

US 2002 120225 (McDaniel) discloses a method for enhancing the transport of an active agent through mammalian skin, comprising: exposing the skin to ultrasound, and applying an active agent to the skin, wherein the step of applying an active agent to the skin comprises injecting the active agent into the skin, and wherein the active agent comprises at least one of Vitamin C, Vitamin E, Vitamin A, Vitamin K, Vitamin F, Retin A (Tretinoin), Adapalene, Retinol, Hydroquinone, Kojic acid, a growth factor, *echinacea*, an antibiotic, an antifungal, an antiviral, a bleaching agent, an alpha hydroxy acid, a beta hydroxy acid, salicylic acid, antioxidant triad compound, a seaweed derivative, a salt water derivative, an antioxidant, a phytoanthocyanin, a phytonutrient, a botanical product, a herbaceous product, a hormone, an enzyme, a mineral, a genetically engineered substance, a cofactor, a catalyst, an antiaging substance, insulin, trace elements, minerals, Rogaine, a hair growth stimulating substance, a hair growth inhibiting substance, a dye, a natural or synthetic melanin, a metalloproteinase inhibitor, proline, hydroxyproline, an anesthetic substance.

It has been found that 4-hexylresorcinol in combination with MMP inhibitor galardin synergistically reduces melanin content in melanocytes. The invention thus relates to a composition comprising a synergistic combination of 4-hexylresorcinol and galardin for use in skin lightening. Thus the composition, when applied topically over an appropriate length of time in-vivo, may be used to lighten the skin, or to reduce age spots or freckles.

SUMMARY OF THE INVENTION

Accordingly, in a first aspect, the present invention provides a skin lightening composition comprising an effective amount of 4-hexylresorcinol; and an effective amount of galardin.

In a second aspect, the invention provides use of the composition according to the invention for skin lightening.

In a third aspect, the invention provides a method of lightening the skin of a human, the method comprising the step of applying the composition according to the invention onto the skin.

These and other aspects, features and advantages will become apparent to those of ordinary skill in the art from a reading of the following detailed description and the appended claims. For the avoidance of doubt, any feature of one aspect of the present invention may be utilised in any other aspect of the invention. The word "comprising" is intended to mean "including" but not necessarily "consisting of" or "composed of." In other words, the listed steps or options need not be exhaustive. It is noted that the examples given in the description below are intended to clarify the invention and are not intended to limit the invention to those examples per se. Similarly, all percentages are weight/weight percentages unless otherwise indicated. Except in the operating and comparative examples, or where otherwise explicitly indicated, all numbers in this description indicating amounts of material or conditions of reaction, physical properties of materials and/or use are to be understood as modified by the word "about". Numerical ranges expressed in the format "from x to y" are understood to include x and y. When for a specific feature multiple preferred ranges are described in the format "from x to y", it is understood that all ranges combining the different endpoints are also contemplated.

DETAILED DESCRIPTION OF THE INVENTION

In a first aspect of the invention, a skin lightening composition is provided, the composition comprising 4-hexylresorcinol and galardin.

4-Hexylresorcinol

4-Hexylresorcinol is an organic compound with local anaesthetic and antiseptic properties. Chemically, it is a yellowish-white substituted phenolic compound. The structure of 4-hexylresorcinol used in the current invention is given below:

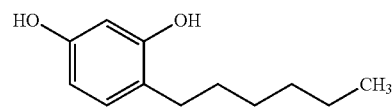

The composition of the present invention comprises an effective amount of 4-hexylresorcinol, typically in a concentration of 0.001 to 10%, preferably at least 0.01%, more preferably at least 0.1%, still more preferably at least 0.25%, even more preferably at least 0.5%, yet more preferably at least 1%, or even at least 2% by weight of the composition;

but preferably not more than 8%, more preferably not more than 6%, still more preferably not more than 5%, yet more preferably not more than 4%, or even not more than 3% by weight of the composition.

Galardin

Galardin also known as GM6001 or ilomastat is a broad-spectrum matrix metalloproteinase inhibitor having the following structure:

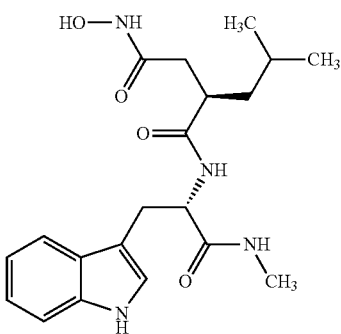 [SMILES: CNC(=O)[C@H](Cc1c[nH]c2ccccc12)NC(=O)[C@@H](CC(=O)NO)CC(C)C]

Galardin is a member of the hydroxamic acid class of reversible matrix metalloproteinase inhibitors. The anionic state of the hydroxamic acid group forms a bidentate complex with the active site zinc.

Matrix metalloproteinases (MMPs) are known for their role in matrix remodeling and are secreted from a variety of cells, including skin cells such as melanocytes, keratinocytes and fibroblast. Galardin is a broad-spectrum synthetic matrix metalloproteinase (MMP) inhibitor, with potent activity against MMP-1, 2, 3, 7, 8, 9, 12, 14, 26. First reported in the 1990s, it has a collagen-like backbone to facilitate binding to the active site of MMPs and a hydroxamate structure (R—CO—NH—OH, where R is an organic residue) which chelates the zinc ion located in the catalytic domain of MMPs. It has been reported to modulate MMPs by preventing the conversion of pro-MMPs into their active form.

Considering that melanin is a group of pigments formed by the oxidation of the amino acid tyrosine, followed by polymerization, it is surprising that galardin also plays a role in the reduction of melanin content in melanocytes together with 4-hexylresorcinol. Additionally galardin also does not appear to have an effect on the inhibition of tyrosinase, which is an oxidase for tyrosine and is a copper containing protein, but not a metalloproteinase, as is demonstrated in the examples herein below.

The present invention highlights the role of galardin in synergistically modulating melanin content in primary human melanocytes by combining with 4-hexylresorcinol.

The composition of the present invention comprises an effective amount of galardin, typically in a concentration of 0.00001 to 10%, preferably at least 0.0001%, more preferably at least 0.001%, still more preferably at least 0.001%, even more preferably at least 0.1%, yet more preferably at least 0.5%, or even at least 1% by weight of the composition; but preferably not more than 8%, more preferably not more than 5%, still more preferably not more than 4%, even more preferably not more than 3%, yet more preferably not more than 2% or even not more than 1.5% by weight of the composition.

Other Ingredients

The composition of the present invention may further comprise a cosmetically acceptable vehicle which may act as diluents, dispersants and/or carriers for the skin lightening agents used in the composition, so as to facilitate their distribution when the composition is applied to the skin. The cosmetically acceptable vehicle suitable for use in the present invention may be aqueous, anhydrous or an emulsion; aqueous or an emulsion, especially water-in-oil or oil-in-water emulsion being most preferred. Water when present typically makes up the balance of the composition. Preferably water is present in a concentration of 5 to 99%, more preferably from 20 to 80%, still more preferably from 40 and 80% by weight of the composition.

Besides water, organic solvents may also serve as carriers within compositions of the present invention.

Emollients may also be used as cosmetically acceptable carriers in the composition of the present invention. Emollients are generally in the form of silicone oils and synthetic esters. Silicone oils may be volatile and non-volatile. Volatile silicone oils are preferably chosen from cyclic or linear polydimethylsiloxanes containing from 3 to 9, preferably from 4 to 5, silicon atoms. Non-volatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes.

Ester emollients that may be used are:
a) Alkenyl or alkyl esters of fatty acids having 10 to 20 carbon atoms. Examples thereof include isoarachidyl neopentanoate, isononyl isonanonoate, oleyl myristate, oleyl stearate, and oleyl oleate.
b) Ether-esters such as fatty acid esters of ethoxylated fatty alcohols.
c) Polyhydric alcohol esters. Ethylene glycol mono- and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.
d) Wax esters such as beeswax, spermaceti, myristyl myristate, stearyl stearate and arachidyl behenate.
e) Sterols esters, of which cholesterol fatty acid esters are examples.

Emollients may be present in the composition anywhere from 0.1 to 50%, preferably from 1 to 20% by weight of the composition.

Fatty acids having from 10 to 30 carbon atoms may also be included as cosmetically acceptable carriers in the composition of this invention. Illustrative examples of such fatty acids are pelargonic, lauric, myristic, palmitic, stearic, isostearic, hydroxystearic, oleic, linoleic, ricinoleic, arachidic, behenic, erucic acids and mixtures thereof.

Humectants of the polyhydric alcohol type may also be employed as cosmetically acceptable carriers in the composition of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol or sodium hyaluronate. The concentration of humectant in the composition may range anywhere from 0.5 to 30%, preferably between 1 and 15% by weight of the composition.

Thickeners may also be utilized as part of the cosmetically acceptable carrier of compositions according to the present invention. Typical thickeners include crosslinked acrylates (e.g. Carbopol 982), hydrophobically-modified acrylates (e.g. Carbopol 1382), cellulosic derivatives and natural gums. Among useful cellulosic derivatives are sodium carboxymethylcellulose, hydroxypropyl methylcellulose, hydroxypropyl cellulose, hydroxyethyl cellulose, ethyl cellulose and hydroxymethyl cellulose. Natural gums suitable for the present invention include guar, xanthan, sclerotium, carrageenan, pectin and combinations of these gums. Concentration of the thickener in the composition may range from 0.0001 to 5%, usually from 0.001 to 1%, optimally from 0.01 to 0.5% by weight.

Collectively the water, solvents, silicones, esters, fatty acids, humectants and/or thickeners will constitute the cosmetically acceptable carrier in amounts from 1 to 99.9%, preferably from 80 to 99% by weight of the composition.

Surfactants may also be present in the composition of the present invention. Total concentration of the surfactant will range from 0.1 to 40%, preferably from 1 to 20%, optimally from 1 to 5% by weight of the composition. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; block copolymers (ethylene oxide/propylene oxide); and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$-$C_{20}$ acyl isethionates, acyl glutamates, $C_8$-$C_{20}$ alkyl ether phosphates and combinations thereof.

Sunscreens include those materials commonly employed to block ultraviolet light. Illustrative compounds are the derivatives of PABA, cinnamate and salicylate. For example, avobenzophenone (Parsol 1789®) octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the compositions can vary depending upon the degree of protection desired from the sun's UV radiation. Additives that reflect or scatter the sun rays may also be employed. These additives include oxides like zinc oxide and titanium dioxide.

The compositions of the present invention can comprise a wide range of other optional components. The CTFA Cosmetic Ingredient Handbook, Second Edition, 1992, which is incorporated by reference herein in its entirety, describes a wide variety of non-limiting cosmetic and pharmaceutical ingredients commonly used in the skin care industry, which are suitable for use in the compositions of the present invention. Examples include: antioxidants, binders, biological additives, buffering agents, colorants, polymers, astringents, fragrance, opacifying agents, conditioners, exfoliating agents, pH adjusters, preservatives, natural extracts, essential oils, skin sensates, skin soothing agents, and skin healing agents.

When making the composition of the present invention, the desired ingredients are mixed in no particular order and usually at temperatures from about 70 to about 80° C. and under atmospheric pressure.

The packaging for the composition of this invention can be a patch, bottle, tube, roll-ball applicator, propellant driven aerosol device, squeeze container or lidded jar.

In a second aspect, the invention relates to use of the composition according to the invention for skin lightening.

In a third aspect, the invention relates to a method of lightening the skin of a human, the method comprising the step of applying the composition according to the invention onto the skin.

The invention will now be illustrated by means of the following non-limiting examples.

EXAMPLES

Example 1: In-Vitro Studies on the Effect of 4-Hexylresorcinol and Galardin on Melanin Inhibition Materials
  (i) Primary human neonatal foreskin melanocytes, Medium 254 and Human Melanocyte Growth Supplement-2 (Life Technologies)
  (ii) Galardin(R)-N4-Hydroxy-N1-[(S)-2-(1H-indol-3-yl)-1-methylcarbamoyl-ethyl]-2-isobutyl-succinamide (Sigma-Aldrich)
  (iii) Nicotinamide (Sigma Aldric)
  (iv) Hexylresorcinol (Sigma Aldrich)
  (v) Calcein-AM—Calcein acetoxymethyl ester (Sigma Aldrich)
  (vi) DMSO—Dimethyl sulfoxide (Sigma Aldrich)
  (vii) Sodium hydroxide (Merck Specialities Pvt. Ltd.)
  (viii) HEPES-(4-(2-Hydroxyethyl)piperazine-1-ethanesulfonic acid, N-(2-Hydroxyethyl)piperazine-N'-(2-ethanesulfonic acid) (Sigma Aldrich)
  (ix) NaCl—Sodium chloride (Fisher Scientific)
  (x) NP40—Nonidet P 40 (USB Corporation)
  (xi) PMSF—Phenylmethanesulfonyl fluoride (Sigma-Aldrich)
  (xii) Protease inhibitor cocktail (Sigma-Aldrich)
  (xiii) L-Tyrosine (Sigma-Aldrich)
Methods
  (i) Cell Cultures:
  Neonatal foreskin primary human melanocytes were procured from Life Technologies, USA. Cells were grown in Medium 254 supplemented with human melanocyte growth supplement-2 and maintained at 37° C. in a humidified incubator with 5% CO2 atmosphere. The maintenance and sub culturing of cells were carried out as per the manufacturer's instructions. Cells between passages 3-6 were used for experimentation.
  (ii) Active Addition:
  Cells were seeded at a density of 5×104/well in a 24 well plate in Melanocyte Growth Media (MGM) and incubated for 24 hrs at 37° C./5% $CO_2$. Actives were added to cells along with relevant controls. 72 hrs post active treatment, cell viability was determined using the Calcein method followed by measurement of cellular melanin content (described in below sections).

(iii) Cell Viability Assay:
Briefly, spent media was removed and cells washed once with 0.2 ml of 1× PBS-Ca—Mg solution. Fresh 1 µM calcein-AM in PBS buffer was added to each well. Plates were incubated for 30 min. at 37° C. in a $CO_2$ incubator. Calcein fluorescence was then measured (excitation at 490 nm and emission at 520 nm) in TECAN M1000 plate reader.

(iv) Melanin Content Assay:
After Calcein measurements, cultures were rinsed with PBS (1×) and lysed for 1 hour at 60° C. in a shaker incubator using NaOH/DMSO mix. Melanin content was measured in a Tecan plate reader (405 nm filter), corrected for cell numbers and represented as % inhibition.

(v) In Vitro Human Tyrosinase Activity Assay:
Primary human melanocytic lysate was used as a source of Tyrosinase enzyme. Human melanocytic lysate and test actives (at different concentrations) were incubated together for 15 mins, prior to addition of Tyrosine/DOPA substrate mix. Assay plate was then incubated at 37° C. for ~14-16 hrs. Optical Density was measured at 405 nm and % inhibition of Tyrosinase activity calculated.

Results

TABLE I

| Treatments | Average % inhibition of cellular melanin | SE |
| --- | --- | --- |
| DMSO 0.1% | 0 | 0 |
| 1 uM Galardin | 7 | 3 |
| 10 uM Galardin | 17 | 4 |
| 1 uM 4-HR | 11 | 3 |
| 10 uM 4-HR | 38 | 2 |
| DMSO 0.2% | 0 | 0 |
| 1 uM 4-HR + 1 uM GD | 24 | 5 |
| 1 uM 4-HR + 10 uM GD | 30 | 3 |
| 10 uM 4-HR + 1 uM GD | 50 | 3 |

TABLE II

| Treatments | Average % inhibition in Tyrosinase enzyme activity | SE |
| --- | --- | --- |
| No enzyme control | 100 | 0 |
| 50 µM GD | −20 | 11 |
| 10 µM GD | −2 | 14 |
| 5 µM GD | −3 | 15 |
| 1 µM GD | −1 | 10 |
| 50 µM 4-HR | 78 | 11 |
| 10 µM 4-HR | 78 | 8 |
| 5 µM 4-HR | 55 | 15 |
| 1 µM 4-HR | 28 | 4 |

CONCLUSION

The above table (table I) highlights the synergistic reduction of melanin content obtained by combining galardin with 4-hexylresorcinol. The data in table I show that galardin by itself gave either no reduction (at 1 µM) or modest reduction (at 10 µM) of melanin content in primary human melanocytes while 4-hexylresorcinol gave significant reduction in melanin content. However, when galardin and 4-hexylresorcinol were combined together in different ratios, synergistic reduction in melanin content was obtained at specific tested concentrations of each active which was higher than the additive effect of their individual reduction.

Table II further illustrates that reduction in melanin content was not through direct modulation of Tyrosinase enzyme activity for galardin but for 4-hexylresorcinol it was through direct modulation of Tyrosinase enzyme activity.

The invention claimed is:

1. A skin lightening composition comprising
   a) an effective amount of 4-hexylresorcinol; and
   b) an effective amount of galardin.

2. The skin lightening composition according to claim 1 wherein the composition comprises 0.00001 to 10% by weight of galardin.

3. The skin lightening composition according to claim 1 wherein the composition comprises 0.001 to 10% by weight of hexylresorcinol.

4. The skin lightening composition according to claim 1, further comprising an additional skin lightening agent.

5. The skin lightening composition according to claim 1 in the form of a topical composition.

6. A method of lightening the skin of a human, the method comprising the step of applying the composition according to claim 1 onto the skin.

* * * * *